United States Patent [19]

Ishihara et al.

[11] Patent Number: 4,588,832
[45] Date of Patent: May 13, 1986

[54] METHOD FOR THE PREPARATION OF A 1-ALKYNYLSILYL COMPOUND

[75] Inventors: Toshinobu Ishihara; Akira Yamamoto; Minoru Takamizawa, all of Niigata, Japan

[73] Assignee: Shin-Etsu Chemical Co., Ltd., Tokyo, Japan

[21] Appl. No.: 682,267

[22] Filed: Dec. 17, 1984

[30] Foreign Application Priority Data

Dec. 16, 1983 [JP] Japan .............................. 58-237520

[51] Int. Cl.$^4$ .............................................. C07F 7/08
[52] U.S. Cl. .................................................... 556/478
[58] Field of Search ......................................... 556/478

[56] References Cited

U.S. PATENT DOCUMENTS 2,927,004 3/1960 Girardot .......................... 556/478 X
3,249,630 5/1966 Viehe ............................. 556/478 X

*Primary Examiner*—Paul F. Shaver
*Attorney, Agent, or Firm*—Toren, McGeady, Stanger, Goldberg & Kiel

[57] ABSTRACT

The invention provides a novel and economical route for the synthetic preparation of a 1-alkynyl trihydrocarbyl silane compound. The method comprises the steps of reacting metallic sodium with a hydrocarbyl-substituted acetylene or allene compound to form a substituted sodium acetylide and reacting the acetylide with a trihydrocarbyl monohalogenosilane in the reaction mixture which is admixed with a polar organic solvent such as dimethylformamide.

9 Claims, No Drawings

METHOD FOR THE PREPARATION OF A 1-ALKYNYLSILYL COMPOUND

BACKGROUND OF THE INVENTION

The present invention relates to a novel method for the preparation of a 1-alkynylsilyl compound or 1-alkynyl silane compound.

1-Alkynylsilyl compounds are useful as an intermediate for the synthetic preparation of various kinds of silicon-containing organic compounds. Several methods are known in the prior art for the preparation of such a 1-alkynylsilyl compound and the most typical among them is the method disclosed in Journal of the American Chemical Society, volume 74, page 4853 (1952) and Doklady Akademii Nauk S.S.S.R., volume 93, page 293 (1953), according to which a Grignard reagent 1-alkynylmagnesium bromide prepared from a 1-alkyne compound and ethylmagnesium bromide is reacted with a trihydrocarbyl monochlorosilane to cause substitution of the 1-alkynyl group for the silicon-bonded chlorine atom in the strating silane whereby a trihydrocarbyl 1-alkynylsilane is obtained.

This method is, however, not satisfactory as an industrial process because the production cost of the desired compound is high due to the low availability and expensiveness of the starting 1-alkyne compound and to the large loss of the solvent or difficulty in the recovery of the solvent which is a water-soluble solvent such as tetrahydrofuran.

SUMMARY OF THE INVENTION

An object of the present invention is therefore to provide a novel and economical method for the synthetic preparation of a 1-alkynylsilyl compound or, in particular, 1-alkynyl silane compound free from the above described problems and disadvantages in the prior art methods.

Thus, the method of the present invention for the preparation of a 1-alkynylsilyl compound comprises the steps of:

(a) reacting a hydrocarbyl-substituted acetylene compound represented by the general formula $R^1C\equiv CH$, in which $R^1$ is a monovalnet hydrocarbon group, or a substituted or unsubstituted allene compound represented by the general formula $R^2CH=C=CH_2$, in which $R^2$ is a hydrogen atom or a monovalent hydrocarbon group, with metallic sodium in an inert organic solvent to form a substituted sodium acetylide in the reaction mixture;

(b) admixing the reaction mixture with an organic polar solvent; and (c) admixing the reaction mixture containing the substituted sodium acetylide and the organic polar solvent with a trihydrocarbyl monohalogenosilane represented by the general formula $R_3SiX$, in which X is a halogen, e.g. chlorine, atom and R is a substituted or unsubstituted monovalent hydrocarbon group each independent from the others.

The 1-alkynylsilyl compound obtained by the above described method is represented by the general formula of either $R^1C\equiv CSiR_3$ or $R^2CH_2C\equiv CSiR_3$, in which R, $R^1$ and $R^2$ each have the meaning as defined above, according to the type of the starting compound which may be the hydrocarbyl-substituted acetylene compound or the substituted or unsubstituted allene compound, respectively.

DETAILED DESCRIPTION OF THE PREFERRED EMBODIMENTS

In the above described method of the present invention, the starting material may be a relatively inexpensive dienic compound such as allene, 1,2-butadiene and the like obtained in large quantities in the petrochemical industry and no disadvantageous loss of the solvent is involved in the process so that the desired 1-alkynylsilyl compound can be produced with an outstandingly low cost.

The atarting material in the inventive method belonging to one of the alternative classes is a hydrocarbyl-substituted acetylene compound represented by the general formula $R^1$-CH, in which $R^1$ is a monovalent hydrocarbon group such as alkyl, aryl and alkenyl groups. Particular examples of such a hydrocarbyl-substituted acetylene compound include alkylacetylenes such as methylacetylene and ethylacetylene, arylacetylenes such as phenylacetylene and tolylacetylenes and alkenylacetylenes such as 4-hexen-1-yne. The starting material of the other class is a substituted or unsubstituted allene compound represented by the general formula $R^2CH=C=CH_2$, in which $R^2$ is a hydrogen atom or a monovalent hydrocarbon group which can be an alkyl or aryl group. Particular examples of such an allene compound include allene, 1,2-butadiene and 1,2-pentadiene.

The first step of the inventive method is the reaction of the above described starting compound with metallic sodium in an inert organic solvent to form a substituted sodium acetylide. The inert organic solvent should be an aromatic hydrocarbon solvent such as toluene and xylene, an aliphatic hydrocarbon solvent such as heptane and octane or an ether solvent such as dibutyl ether and diphenyl ether. The reaction is performed with introduction of the starting unsaturated compound, i.e. substituted acetylene or substituted or unsubstituted allene compound, by dropwise addition or by bubbling into a fine dispersion of metallic sodium in the inert organic solvent. The concentration of the metallic sodium in the organic solvent should be such that from 100 to 1000 g or, preferably, from 200 to 400 g of the organic solvent contain 1 mole, i.e. 23 g, of metallic sodium. The overall amount of metallic sodium in the dispersion should be in the range from 0.3 to 1 mole or, preperably, from 0.5 to 0.7 mole per mole of the starting unsaturated compound to be introduced into the dispersion of the metallic sodium. The reaction temperature should be in the range from 80° to 130° C. or, preferably, from 95° to 115° C. More preferably, the reaction is performed at a temperature higher than 97° C. which is the melting point of metallic sodium because the reaction velocity is greatly increased when the metallic sodium is in the molten state. A reaction temperature higher than 130° C. should be avoided because the substituted sodium acetylide as the reaction product may be decomposed at such a high temperature.

The next step of the inventive method is the reaction of the thus formed substituted sodium acetylide with a trihydrocarbyl monohalogenosilane or a trihydrocarbylsilyl halide of the formula $R_3SiX$, in which R and X each have the meaning defined above. In this case, it is essential that the reaction is performed in the presence of a polar organic solvent which is selected from the class consisting of dimethylformamide, dimethylacetamide, dimethyl sulfoxide, hexamethyl phosphoric triamide and the like. The amount of such a polar organic solvent to be added to the reaction mixture should be in the range from 1 to 10 parts by weight per 100 parts by weight of the inert organic solvent used in the first step and contained in the reaction mixture.

The monovalent hydrocarbon group denoted by R in the general formula $R_3SiX$ for the trihydrocarbyl monohalogenosilane as one of the reactants is selected from the class consisting of alkyl, aryl and alkenyl groups. Substituted monovalent hydrocarbon groups obtained by the replacement of a part or all of the hydrogen atoms in the above named classes of hydrocarbon groups with substituents such as halogen atoms and cyano groups are also suitable. Particular examples of such a silane compound include trimethyl chlorosilane, triethyl chlorosilane, dimethyl propyl chlorosilane, dimethyl phenyl chlorosilane, dimethyl vinyl chlorosilane, dimethyl chloromethyl chlorosilane and the like.

The silylation reaction of the substituted sodium acetylide is performed by adding such a silane compound to the reaction mixture containing the acetylide and admixed with the above mentioned polar organic solvent. The amount of the silane compound should preferably be in the range from 0.8 to 1.2 moles per mole of the substituted sodium acetylide in the reaction mixture. The reaction temperature is preferably in the range from about 20° C. to about 60° C.

The 1-alkynylsilyl compound obtained by the method of the present invention is useful as an intermediate in the synthesis of an organic compound having a specific geometrically isomeric structure by virtue of the characteristic triple bond in the molecule so that the compound is industrially important in the manufacture of various kinds of biologically active compounds including medicines and agricultural chemicals. Further, such a compound is also useful as a monomeric compound in the preparation of organic semiconductors, gas-permeable polymeric materials and the like.

In the following, the method of the present invention is described in more detail by way of examples.

EXAMPLE 1

Into a reaction flask of 500 ml capacity were introduced 250 g of xylene and 23 g of metallic sodium which was finely dispersed in xylene to have a particle diameter of 20 μm or smaller. This reaction mixture was heated and kept at a temperature of 100° to 110° C. and gaseous 1,2-butadiene was introduced thereinto for 1 hour at a rate of 1 liter/minutes to give sodium ethylacetylide quantitatively.

The mixture of sodium ethylacetylide in xylene was admixed with 10 g of dimethylformamide and 108.5 g of trimethyl chlorosilane were added dropwise into the reaction mixture at 40° to 50° C. over a period of 1 hour. After completion of the dropwise addition of the silane, the reaction mixture was further agitated for additional 1 hour keeping the temperature at 50° C. and then poured into 200 ml of a 20% hydrochloric acid. The organic solution was taken by phase seperation and distilled to give 118 g of trimethyl 1-butynylsilane. The yield was 93.7% based on the amount of the metallic sodium.

EXAMPLE 2

The experimental procedure was substantially the same as in Example 1 excepting the dropwise addition of 153 g of phenylacetylene in place of the introduction of the gaseous 1,2-butadiene to give 132 g of trimethyl phenylethynyl silane. This yield was 88% of the theoretical value based on the amount of the metallic sodium.

What is claimed is:

1. A method for the preparation of a 1-alkynylsilyl compound which comprises the steps of:
   (a) reacting a hydrocarbyl-substituted acetylene compound represented by the general formula $R^1C\equiv CH$, in which $R^1$ is a monovalent hydrocarbon group, or a substituted or unsubstituted allene compound represented by the general formula $R^2CH=C=CH_2$, in which $R^2$ is a hydrogen atom or a monovalent hydrocarbon group, with metallic sodium in an inert organic solvent to form a substituted sodium acetylide in the reaction mixture;
   (b) admixing the reaction mixture with an organic polar solvent; and
   (c) admixing the reaction mixture with a trihydrocarbyl monohalogenosilane represented by the general formula $R_3SiX$, in which X is a halogen atom and R is a substituted or unsubstituted monovalent hydrocarbon group each independent from the others.

2. The method as claimed in claim 1 wherein the inert organic solvent used in the step (a) is selected from the class consisting of aromatic hydrocarbons, aliphatic hydrocarbons and ether compounds.

3. The method as claimed in claim 1 wherein the amount of the inert organic solvent used in the step (a) is in the range from 100 to 1000 g per mole of the metallic sodium.

4. The method as claimed in claim 1 wherein the amount of the metallic sodium is in the range from 0.3 to 1 mole per mole of the hydrocarbyl-substituted acetylene compound or substituted or unsubstituted allene compound.

5. The method as claimed in claim 1 wherein the reaction temperature in the step (a) is in the range from 80° to 130° C.

6. The method as claimed in claim 1 wherein the polar organic solvent admixed in the step (b) is selected from the class consisting of dimethylformamide, dimethylacetamide, dimetyl sulfoxide and hexafluorophosphoric triamide.

7. The method as claimed in claim 1 wherein the amount of the polar organic solvent is in the range from 1 to 10 parts by weight per 100 parts by weight of the inert organic solvent.

8. The method as claimed in claim 1 wherein the amount of the trihydrocarbyl monohalogenosilane is in the range from 0.8 to 1.2 moles per mole of the substituted sodium acetylide contained in the reaction mixture.

9. The method as claimed in claim 1 wherein the reaction temperature in the step (c) is in the range from 20° to 60° C.

* * * * *